US012622998B2

(12) United States Patent
Chen et al.

(10) Patent No.: US 12,622,998 B2
(45) Date of Patent: May 12, 2026

(54) LIQUID DRESSING

(71) Applicant: TRONJEN MEDICAL TECHNOLOGY INC., Taichung City (TW)

(72) Inventors: Szu-Hsien Chen, Taichung (TW); Ya-Wen Ku, Taichung (TW); Yen-Hsuan Liu, Taichung (TW)

(73) Assignee: TRONJEN MEDICAL TECHNOLOGY INC., Taichung City (TW)

( * ) Notice: Subject to any disclaimer, the term of this patent is extended or adjusted under 35 U.S.C. 154(b) by 946 days.

(21) Appl. No.: 17/691,660

(22) Filed: Mar. 10, 2022

(65) Prior Publication Data

US 2023/0035312 A1　Feb. 2, 2023

(30) Foreign Application Priority Data

Jul. 20, 2021　(TW) ................................. 110126615

(51) Int. Cl.
| | |
|---|---|
| *A61L 26/00* | (2006.01) |
| *C08G 18/10* | (2006.01) |
| *C08G 18/48* | (2006.01) |
| *C08G 18/73* | (2006.01) |
| *C08G 77/16* | (2006.01) |
| *C08G 77/18* | (2006.01) |

(52) U.S. Cl.
CPC .......... *A61L 26/0019* (2013.01); *C08G 18/10* (2013.01); *C08G 18/4833* (2013.01); *C08G 18/73* (2013.01); *C08G 77/16* (2013.01); *C08G 77/18* (2013.01)

(58) Field of Classification Search
None
See application file for complete search history.

(56) References Cited

U.S. PATENT DOCUMENTS

| | | | | |
|---|---|---|---|---|
| 2014/0194838 A1* | 7/2014 | Wibaux | ................ | A61L 15/225 523/105 |
| 2017/0049926 A1* | 2/2017 | Langer-Anderson | ........................ | A61L 24/0015 |

FOREIGN PATENT DOCUMENTS

TW　　　　I707930 B　　10/2020

OTHER PUBLICATIONS

Sigma Aldrich product web page for hexamethyldisilazane (2025). Obtained from <https://www.sigmaaldrich.com/US/en/product/aldrich/440191?srsltid=AfmBOoofMkU9KDYylfYh-cwdIBmbIQJ-hGSZOmERKTneluUrFaKE0GhN>.*
Search Report appended to an Office Action, which was issued to Taiwanese counterpart Application No. 110126615 by the TIPO on Nov. 25, 2021 with an English translation thereof.

* cited by examiner

*Primary Examiner* — Anna R Falkowitz
*Assistant Examiner* — Garen Gotfredson
(74) *Attorney, Agent, or Firm* — LAW OFFICES OF ALBERT WAI-KIT CHAN, PLLC

(57) ABSTRACT

A liquid dressing includes a solvent and a film-forming polymer that is dissolved in the solvent and that is made by a process including: providing an alkoxy group-containing silicone resin which is obtained by subjecting an orthosilicate compound and an acidic aqueous solution to a hydrolysis and polymerization reaction; providing an isocyanate group-containing prepolymer which is obtained by reacting a diisocyanate compound with a hydrophilic polyether diol; and subjecting the alkoxy group-containing silicone resin and the isocyanate group-containing prepolymer to a polymerization reaction so as to obtain the film-forming polymer.

9 Claims, 2 Drawing Sheets

(A)

(B)

(C)

LIQUID DRESSING

CROSS-REFERENCE TO RELATED APPLICATION

This application claims priority of Taiwanese Invention Patent Application No. 110126615, filed on Jul. 20, 2021.

FIELD

The present disclosure relates to a liquid dressing, and more particularly to a liquid dressing containing a polysiloxane-polyurethane copolymer.

BACKGROUND

In order to facilitate recovery of an open wound such as skin incision or abrasion, great care of the open wound (for example, reducing its exposure to external stimuli (e.g., water or dirt) would be required. Moreover, the breathability, ease of use and comfort of touch regarding a dressing material used for protecting the open wound should also be taken into account.

CN 109200333 A discloses a skin protective liquid composition that can be sprayed onto the skin to form a non-irritant skin protection film. The skin protective liquid composition is made from a linear polymer compound that has a polyphenylhydroxysiloxane structure, and that is dissolved in a solvent. However, after being sprayed, the skin protective liquid composition would easily clog the nozzle of the spray bottle, causing inconvenience in use of such skin protective liquid composition. If the spray bottle containing the skin protection liquid composition is filled with a pressurized gas, there might be a risk of danger during transportation.

SUMMARY

Therefore, the present disclosure provides a liquid dressing which can alleviate at least one of the drawbacks of the prior art.

The liquid dressing includes a solvent and a film-forming polymer dissolved in the solvent. The film-forming polymer is made by a process including:

providing an alkoxy group-containing silicone resin which is obtained by subjecting an orthosilicate compound and an acidic aqueous solution to a hydrolysis and polymerization reaction;

providing an isocyanate group-containing prepolymer which is obtained by reacting a diisocyanate compound with a hydrophilic polyether diol; and subjecting the alkoxy group-containing silicone resin and the isocyanate group-containing prepolymer to a polymerization reaction so as to obtain the film-forming polymer.

BRIEF DESCRIPTION OF THE DRAWINGS

Other features and advantages of the present disclosure will become apparent in the following detailed description of the embodiments with reference to the accompanying drawings, of which.

DETAILED DESCRIPTION

Figure 1:
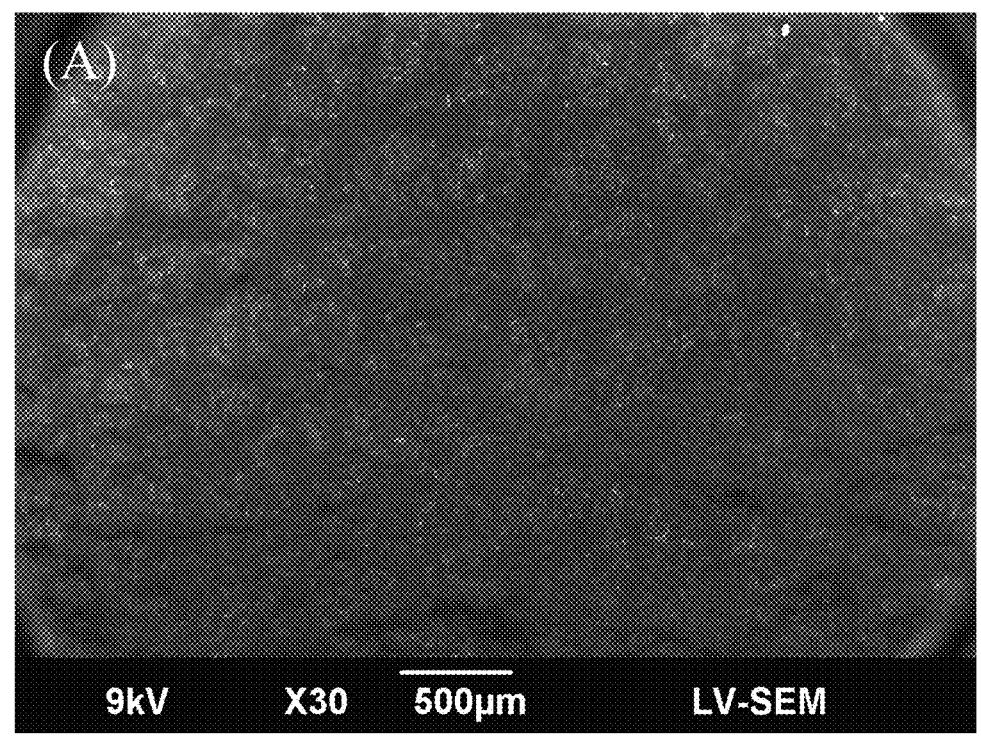
FIG. 1 shows scanning electron microscopy images of a first polypropylene tape applied to the skin (A) before spraying the liquid dressing of Example 1, and a second polypropylene tape applied to the skin (B) after spraying the liquid dressing in Example 1, infra.
Figure 1:
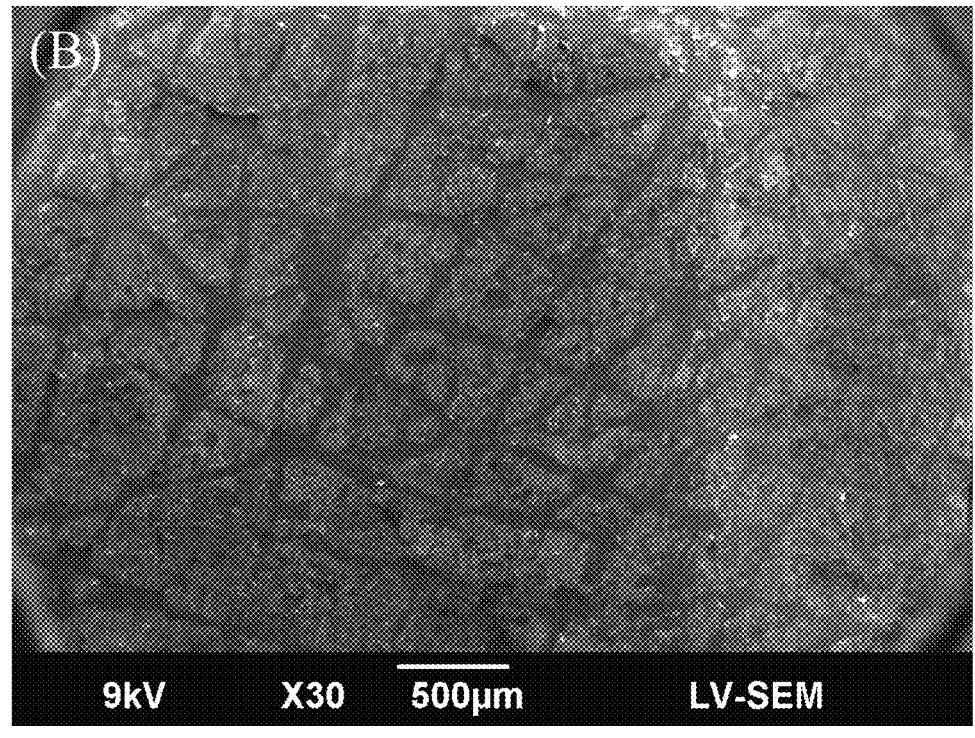

It is to be understood that, if any prior art publication is referred to herein, such reference does not constitute an admission that the publication forms a part of the common general knowledge in the art, in Taiwan or any other country.

For the purpose of this specification, it will be clearly understood that the word "comprising" means "including but not limited to", and that the word "comprises" has a corresponding meaning.

Unless otherwise defined, all technical and scientific terms used herein have the meaning commonly understood by a person skilled in the art to which this disclosure belongs. One skilled in the art will recognize many methods and materials similar or equivalent to those described herein, which could be used in the practice of this disclosure. Indeed, this disclosure is in no way limited to the methods and materials described.

The present disclosure provides a liquid dressing which includes a solvent and a film-forming polymer dissolved in the solvent. The film-forming polymer is made by a process including:

providing an alkoxy group-containing silicone resin which is obtained by subjecting an orthosilicate compound and an acidic aqueous solution to a hydrolysis and polymerization reaction;

providing an isocyanate group-containing prepolymer which is obtained by reacting a diisocyanate compound with a hydrophilic polyether diol; and subjecting the alkoxy group-containing silicone resin and the isocyanate group-containing prepolymer to a polymerization reaction so as to obtain the film-forming polymer.

In certain embodiments, the orthosilicate compound is selected from the group consisting of tetraethyl orthosilicate (TEOS), tetramethyl orthosilicate (TMOS), and a combination thereof.

In certain embodiments, the solvent is hexamethyldisilazane (HMDS).

In certain embodiments, the diisocyanate compound is selected from the group consisting of hexamethylene diisocyanate (HDI), dicyclohexylmethane-4,4'-diisocyanate ($H_{12}$MDI), isophorone diisocyanate (IPDI), and combinations thereof.

In certain embodiments, the hydrophilic polyether diol is polyethylene glycol (PEG). In an exemplary embodiment, the polyethylene glycol has a weight average molecular weight ranging from 400 g/mol to 2000 g/mol. In another exemplary embodiment, the polyethylene glycol has a weight average molecular weight ranging from 500 g/mol to 1000 g/mol.

In certain embodiments, a molar ratio of the orthosilicate compound to water in the acidic aqueous solution ranges from 1:3.5 to 1:3.9.

In certain embodiments, a molar ratio of the diisocyanate compound to the hydrophilic polyether diol ranges from 1.1:1 to 1.5:1.

In certain embodiments, the alkoxy group-containing silicone resin has a weight average molecular weight ranging from 10000 g/mol to 30000 g/mol.

In certain embodiments, the film-forming polymer is free from an aromatic ring structure.

In certain embodiments, the acidic aqueous solution is selected from the group consisting of an aqueous acetic acid solution, an aqueous hydrochloric acid solution and an aqueous phosphoric acid solution. In an exemplary embodiment, the acidic aqueous solution has a pH value ranging from 3 to 5.

The present disclosure will be further described by way of the following examples. However, it should be understood that the following examples are intended solely for the purpose of illustration and should not be construed as limiting the present disclosure in practice.

EXAMPLES

Example 1

Tetraethyl orthosilicate (TEOS) was mixed with an aqueous hydrochloric acid solution (pH value of which ranged from 4 to 5) at a molar ratio of 1:3.6 (TEOS:$H_2O$) to obtain a mixture. The mixture was subjected to a hydrolysis and polycondensation reaction at 50° C. for 24 hours, followed by adding 0.1 M of an aqueous sodium hydroxide solution to reach a pH value of 7 so as to terminate the reaction, thereby obtaining an ethoxy group- and hydroxyl group-containing silicone resin. The silicone resin had a weight average molecular weight of 10000 g/mol, and had a partially cross-linked network.

Meanwhile, hexamethylene diisocyanate (HDI) was mixed with polyethylene glycol (PEG) having a weight average molecular weight of 1000 g/mol (also referred to as PEG 1000) at a molar ratio of 1.3:1 to obtain a mixture. The mixture was allowed to react at 80° C. for 1 hour, thereby obtaining an isocyanate group-containing prepolymer.

The ethoxy group- and hydroxyl group-containing silicone resin and the isocyanate group-containing prepolymer were mixed at a molar ratio of 1:1. The polymerization reaction was allowed to proceed at 80° C. for 2 hours, thereby obtaining a film-forming polymer.

Thereafter, 5 g to 10 g of the film-forming polymer was dissolved in 100 g of hexamethyldisilazane (HMDS), so as to obtain a polysiloxane-polyurethane copolymer-containing liquid dressing of Example 1.

Comparative Example 1

The liquid dressing of Comparative Example 1 was SENSI-CARE® Sting Free Skin Barrier Spray that was purchased from ConvaTec Group plc (Catalogue no: 420790).

Comparative Example 2

The liquid dressing of Comparative Example 2 was synthesized according to the preparation procedures and conditions for Sample 2 that is disclosed in CN 109200333 A.

Comparative Example 3

The liquid dressing of Comparative Example 3 was Cavilon™ No Sting Barrier Film Spray that was purchased from 3M Company (Catalogue no: 3346E).

Property Evaluation:
1. Electron Microscopy Examination

A first polypropylene tape was placed on a 3 cm×3 cm designated area of the skin on the inner arm and then removed. Liquid dressing of Example 1 was placed into a spray bottle, and then 0.3 mL of the liquid dressing of Example 1 was sprayed onto the aforesaid designated area. After waiting for 10 seconds for the liquid dressing of Example 1 to form a transparent film, a second polypropylene tape was placed and pressed onto the transparent film at the designated area of the skin for 5 minutes, followed by removing the second polypropylene tape. The first and second polypropylene tapes were subjected to a gold coating process for 1 minute using a SPI-Module™ Sputter Coater (Manufacturer: Structure Probe, Inc.; Model no.: 11427-AB). Thereafter, the first and second polypropylene tapes were observed and photographed under a low vacuum scanning electron microscope (LV-SEM) (Manufacturer: JEOL, Ltd.; Model no.: JSM-6390LV). SEM images of the first and second polypropylene tapes are respectively shown in FIGS. 1(A) and 1(B).

As shown in FIGS. 1(A) and 1(B), a scaly texture of the outermost skin layer was observed both on the first and second polypropylene tapes (which were applied onto the designated area of the skin before and after spraying the liquid dressing of Example 1 onto the designated area of the skin, respectively), indicating that the liquid dressing of Example 1 containing a polysiloxane-polyurethane copolymer would not adversely affect the breathability of the skin.

2. Water Resistance Assessment

The liquid dressings of Example 1 and Comparative Examples 1 and 2 were respectively placed into 3 spray bottles. The respective liquid dressing was then sprayed 6 times towards a piece of toilet paper (i.e., three pieces of toilet paper were respectively sprayed with the three liquid dressings), so that the respective liquid dressing was evenly sprayed onto the toilet paper. Then, the respective liquid dressing on the toilet paper was left to stand for 5 minutes to be dried so as to form a transparent film on the toilet paper. Thereafter, the toilet paper was laid flat, and a water-containing dropper was used to dispense water droplets on the area of the toilet paper sprayed with the respective liquid dressing so as to observe whether the water droplets could penetrate through the toilet paper. Photographs of the three pieces of toilet paper (which were sprayed with the liquid dressings of Example 1 and Comparative Examples 1 and 2, respectively, and were subjected to water dispensing) are respectively shown in FIGS. 2(A), 2(B) and 2(C).

Figure 2:
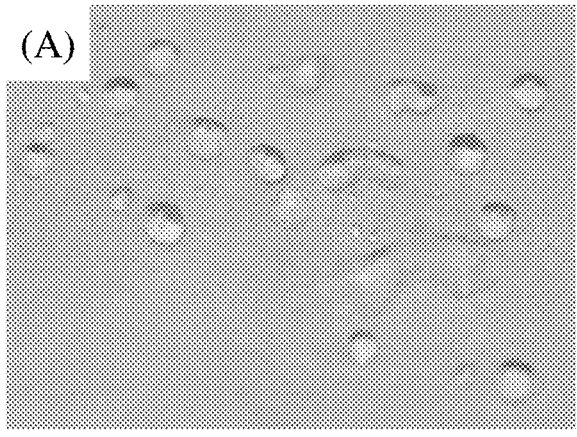
FIG. 2 shows photographs of pieces of toilet paper with water droplets dispensed thereon after being respectively sprayed with (A) the liquid dressing of Example 1, (B) the liquid dressing of Comparative Example 1, and (C) the liquid dressing of Comparative Example 2.
Figure 2:
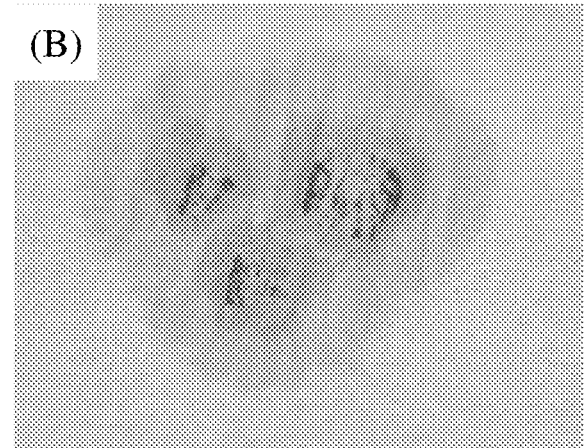
Figure 2:
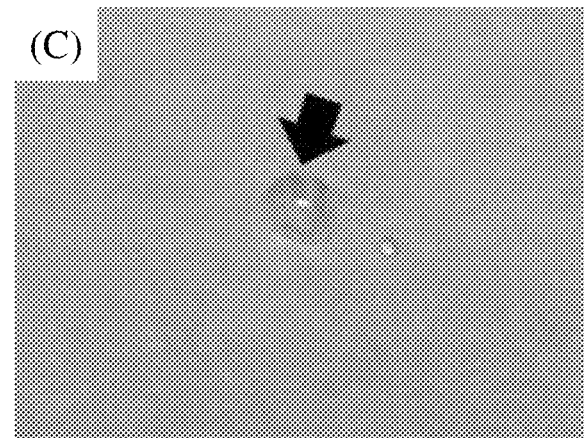

As shown in FIG. 2(A), the toilet paper sprayed with the liquid dressing of Example 1 was not at all penetrated by the water droplets, and the water droplets maintained their bead-like shape. As shown in FIG. 2(B), the water droplets clearly penetrated the toilet paper sprayed with the liquid dressing of Comparative Example 1, causing such toilet paper to be completely wet. As shown in FIG. 2(C), the toilet paper sprayed with the liquid dressing of Comparative Example 2 was slightly penetrated by the water droplets that maintained their bead-like shape, and the area of the toilet paper beneath the water droplets became partially wet (see the pointed arrow).

3. Nozzle Clogging Test

The liquid dressings of Example 1 and Comparative Examples 1 and 2 were respectively placed into spray bottles (each including a spring with a suction straw, a bottle body made from aluminum, an aerosol spray valve made from aluminum, and a nozzle made from plastic and having an aperture with a diameter ranging from 0.3 mm to 0.35 mm so as to produce a spray volume ranging from 0.1 mL to 0.12 mL per stroke). The nozzle of the respective spray bottle was pressed 5 times for spraying the corresponding liquid dressing. Next, the respective spray bottle was left for 2 weeks, after which the nozzle was continuously pressed so as to observe whether the corresponding liquid dressing could be sprayed smoothly, whether the nozzle had delayed rebound, and whether the size of the sprayed area and the amount of the corresponding liquid dressing sprayed had altered (i.e., the smoothness of spraying was hence determined).

The results show that, when the nozzles of the spray bottles containing the liquid dressing of Example 1 were pressed continuously for spraying after being left for two weeks, only about 1% of the spray bottles containing the liquid dressing of Example 1 could not perform spraying smoothly, and such problem could be immediately solved by wiping the nozzle with an alcohol swab, indicating that the liquid dressing of Example 1 containing a polysiloxane-polyurethane copolymer would not clog the nozzles of the spray bottles despite being continuously sprayed. In addition, when the nozzles of the spray bottles containing the liquid dressing of Comparative Example 1 were pressed continuously for spraying after being left for two weeks, approximately 67% of the spray bottles containing the liquid dressing of Comparative Example 1 could not perform spraying smoothly, and such problem could not be immediately solved by wiping the nozzle with an alcohol swab. Moreover, when the nozzles of the spray bottles containing the liquid dressing of Comparative Example 2 were pressed continuously for spraying after being left for two weeks, approximately 97% of the spray bottles containing the liquid dressing of Comparative Example 2 could not perform spraying smoothly, and such problem could not be immediately solved by wiping the nozzle with a alcohol swab.

4. Evaluation for Water Vapor Transmission Rate

Three artificial skin membranes, i.e., a first Strat-M® synthetic membrane (Manufacturer: EMD Millipore, thickness: 300 μm) serving as control group, a second Strat-M® synthetic membrane coated with the liquid dressing of Example 1 (distance of spraying: 8 cm; thickness of coating: 50 μm), and a third Strat-M® synthetic membrane coated with the liquid dressing of Comparative Example 3 (distance of spraying: 8 cm; thickness of coating: 50 μm), were respectively fixedly attached to stainless steel containers that were filled with water using stainless steel clamps so as to tightly seal the containers (a total of three stainless steel containers were sealed with a corresponding one of the first, second and third Strat-M® synthetic membrane). Then, the containers were placed in an oven with a temperature set at 32° C. and a relative humidity of 10% for 24 hours, so as to determine the amount of water being retained in the containers. The results show that, the amount of water (expressed as %) retained after the 24 hour-placement in the oven relative to the amount of water before the 24-hour placement in the oven is 100±8% (the control group), 90±15% (the liquid dressing of Example 1), or 95±5% (the liquid dressing of Comparative Example 3).

5. Drying Rate Assessment

A respective one of the liquid dressings of Example 1 and Comparative Example 3 was evenly sprayed onto the skin of the arm (volume of spraying: 0.5 mL; distance of spraying: 10 cm; area of spraying: 3 cm×3 cm). The sprayed area was visually observed until the respective liquid dressing completely dried, i.e., liquid reflection was absent on the skin surface, or no liquid was found to penetrate into a piece of toilet paper placed on the sprayed area. The experiments were performed in triplicates (n=3), and the result shows that the recorded time for complete drying of the liquid dressing of Example 1 and that for complete drying of the liquid dressing of Comparative Example 3 are 8±3 seconds and 20±5 seconds, respectively.

6. Evaluation for Retention Rate without Cleaning

A respective one of the liquid dressings of Example 1 and Comparative Example 3 was evenly sprayed onto the skin of the arm (volume of spraying: 0.5 mL; distance of spraying: 10 cm; area of spraying: 3 cm×3 cm), followed by conducting Fourier transform infrared spectroscopy-attenuated total reflection (FTIR-ATR) analysis with an infrared spectrophotometer so as to determine the Si—O—Si absorbance peak area between $1000 \text{ cm}^{-1}$ to $1100 \text{ cm}^{-1}$ immediately after spraying. Moreover, the same analysis was conducted after 180 seconds and 300 seconds after spraying. The thus obtained Si—O—Si absorbance peak areas of the respective liquid dressing determined after 180 seconds and 300 seconds after spraying (respectively serving as numerators) were compared with that determined immediately after spraying (serving as a denominator), so as to calculate the percentage of the respective liquid dressing remaining on the skin after 180 seconds and 300 seconds of spraying. The experiments were performed in triplicates (n=3), and the results are shown in Table 1 below.

TABLE 1

| Liquid dressing | Percentage remaining 180 seconds after spraying | Percentage remaining 300 seconds after spraying |
| --- | --- | --- |
| Example 1 | 95 ± 10% | 85 ± 5% |
| Comparative example 3 | 75 ± 11% | 68 ± 4% |

7. Evaluation for Retention Rate after Cleaning

A respective one of the liquid dressings of Example 1 and Comparative Example 3 was evenly sprayed onto the skin of the arm (volume of spraying: 0.5 mL; distance of spraying: 10 cm; area of spraying: 3 cm×3 cm), followed by conducting FTIR-ATR analysis with an infrared spectrophotometer so as to determine the Si—O—Si absorbance peak area between $1000 \text{ cm}^{-1}$ to $1100 \text{ cm}^{-1}$ immediately after spraying. Next, the liquid dressings of Example 1 and Comparative Example 3 were subjected to a first cleaning process, in which an antibacterial hand wash purchased from Integrity Believe Leadership Pharmaceutical Co., Ltd. was rubbed by fingers to form foam, the foam was placed onto the skin at the area sprayed with the respective one of the liquid dressings of Example 1 and Comparative Example 3 and was spread by drawing 3 circles, and the foam was removed using water and drying of the skin proceeded. Thereafter, the liquid dressings cleaned off the foam were subjected to the aforesaid FTIR-ATR analysis. Subsequently, the liquid dressings were subjected to a second cleaning process followed by the aforesaid FTIR-ATR analysis, and then to a third cleaning process followed by the FITR-ATR analysis. The procedures for performing the second and third cleaning processes were similar to those of the first cleaning process.

The thus obtained Si—O—Si absorbance peak areas of the respective liquid dressing determined after the first, second and third cleaning processes (respectively serving as numerators) were compared with that determined immediately after spraying (serving as a denominator), so as to calculate the percentage of the liquid dressing remaining on the skin after the first, second and third cleaning processes.

The experiments were performed in triplicates (n=3), and the results are shown in Table 2 below.

TABLE 2

| Liquid dressing | Percentage remaining after the first cleaning process | Percentage remaining after the second cleaning process | Percentage remaining after the third cleaning process |
|---|---|---|---|
| Example 1 | 85 ± 11% | 70 ± 5% | 63 ± 6% |
| Comparative Example 3 | 83 ± 8% | 78 ± 5% | 75 ± 5% |

8. Sensory Test

A respective one of the liquid dressings of Example 1 and Comparative Example 3 was evenly sprayed onto the skin of the arms of 20 users (volume of spraying: 0.5 mL; distance of spraying: 10 cm; area of spraying: cm×3 cm), and the users are allowed to move freely for 5 minutes. After that, each user was required to provide a compliance score for the liquid dressings of Example 1 and Comparative Example 3 based on characteristics such as, absence of unpleasant odor, low visibility of residue, weak feel of foreign matter, low stickiness, and smoothness of touch, in which 1 point was the smallest unit of score, and was given for complete non-compliance, while 6 points were given for complete compliance. The average scores for the abovementioned characteristics of each liquid dressing are shown in Table 3 below.

TABLE 3

| Liquid dressing | Absence of unpleasant odor | Low visibility of residue | Weak feel of foreign matter | Low stickiness | Smoothness of touch |
|---|---|---|---|---|---|
| Example 1 | 5.5 | 4.65 | 4.15 | 5.0 | 4.8 |
| Comparative Example 3 | 1.8 | 3.9 | 1.9 | 1.8 | 2.15 |

In summary, the liquid dressing of the present disclosure (which contains a polysiloxane-polyurethane copolymer), after being sprayed, is capable of forming a transparent film that provides a good protection effect, and is not liable to clog the nozzle of the spray bottle. In addition, after being sprayed on the skin, the transparent film formed from the liquid dressing of the present disclosure does not adversely affect the breathability of the skin, has a fast drying rate, a good adhesion (i.e., a high retention rate achieved within a few minutes and low possibility of peeling off), is easy to use, and has an excellent touch comfort.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

What is claimed is:

1. A liquid dressing, comprising:

a solvent; and a film-forming polymer dissolved in said solvent and made by a process including:

providing an alkoxy group-containing silicone resin which has a partially cross-linked network and which is obtained by subjecting an orthosilicate compound and an acidic aqueous solution to a hydrolysis and polymerization reaction;

providing an isocyanate group-containing prepolymer which is obtained by reacting a diisocyanate compound with a hydrophilic polyether diol; and subjecting said alkoxy group-containing silicone resin and said isocyanate group-containing prepolymer to a polymerization reaction so as to obtain said film-forming polymer, wherein said solvent is hexamethyldisilazane.

2. The liquid dressing as claimed in claim 1, wherein said orthosilicate compound is selected from the group consisting of tetraethyl orthosilicate, tetramethyl orthosilicate, and a combination thereof.

3. The liquid dressing as claimed in claim 1, wherein said diisocyanate compound is selected from the group consisting of hexamethylene diisocyanate, dicyclohexylmethane-4,4'-diisocyanate, isophorone diisocyanate, and combinations thereof.

4. The liquid dressing as claimed in claim 1, wherein said hydrophilic polyether diol is polyethylene glycol.

5. The liquid dressing as claimed in claim 4, wherein said polyethylene glycol has a weight average molecular weight ranging from 400 g/mol to 2000 g/mol.

6. The liquid dressing as claimed in claim 1, wherein a molar ratio of said orthosilicate compound to water in said acidic aqueous solution ranges from 1:3,5 to 1:3.9.

7. The liquid dressing as claimed in claim 1, wherein a molar ratio of said diisocyanate compound to said hydrophilic polyether diol ranges from 1.1:1 to 1.5:1.

8. The liquid dressing as claimed in claim 1, wherein said alkoxy group-containing silicone resin has a weight average molecular weight ranging from 10000 g/mol to 30000 g/mol.

9. The liquid dressing as claimed in claim 1, wherein said film-forming polymer is free from an aromatic ring structure.

* * * * *